United States Patent
Bossi et al.

(10) Patent No.: US 6,848,321 B2
(45) Date of Patent: Feb. 1, 2005

(54) BOND STRENGTH MEASUREMENT SYSTEM USING SHOCK LOADS

(75) Inventors: Richard H. Bossi, Renton, WA (US); Kevin R. Housen, Federal Way, WA (US); William B. Shepherd, Vashon, WA (US); Michael E. Voss, San Diego, CA (US)

(73) Assignee: The Boeing Company, Chicago, IL (US)

( * ) Notice: Subject to any disclaimer, the term of this patent is extended or adjusted under 35 U.S.C. 154(b) by 102 days.

(21) Appl. No.: 10/273,514

(22) Filed: Oct. 18, 2002

(65) Prior Publication Data

US 2003/0079552 A1 May 1, 2003

Related U.S. Application Data

(63) Continuation of application No. 09/981,162, filed on Oct. 17, 2001, now abandoned.

(51) Int. Cl.$^7$ .................................................. G01N 3/24
(52) U.S. Cl. .............................. 73/842; 73/844; 73/845; 73/788
(58) Field of Search ........................ 73/801, 778–788, 73/827, 815, 841–859

(56) References Cited

U.S. PATENT DOCUMENTS

| | | | |
|---|---|---|---|
| 4,397,702 A | | 8/1983 | Klein et al. |
| 4,944,185 A | | 7/1990 | Clark, Jr. et al. |
| 5,468,136 A | * | 11/1995 | Arisato et al. |
| 5,698,787 A | | 12/1997 | Parzuchowski et al. |
| 5,902,935 A | * | 5/1999 | Georgeson et al. |
| 5,907,098 A | | 5/1999 | Tsuboi et al. |
| 6,004,817 A | | 12/1999 | Chamberlain et al. |
| 6,181,431 B1 | * | 1/2001 | Siu |
| 6,234,025 B1 | | 5/2001 | Gieske et al. |

* cited by examiner

*Primary Examiner*—Edward Lefkowitz
*Assistant Examiner*—Alandra Ellington
(74) *Attorney, Agent, or Firm*—Harness Dickey & Pierce P.L.C.

(57) ABSTRACT

A system and method for non-destructively testing the strength of bonded joints, particularly a bonded joint between two composite components, is provided. The method generally includes activating a source of rapid surface pressure application against a bonded assembly containing the bonded joint to create a shock load. The resulting shock load first generates compression and then tension within the bonded joint, along with surface motions proximate the bonded assembly, and a surface motion detector measures the surface motions to determine the minimum strength of the bonded joint. Accordingly, the surface motions are correlated to the strength of the bonded joint. Further, the magnitude of the impact may be adjusted to vary the amount of tension within the bonded joint to correspond with various load conditions.

40 Claims, 2 Drawing Sheets

BOND STRENGTH MEASUREMENT SYSTEM USING SHOCK LOADS

CROSS-REFERENCE TO RELATED APPLICATIONS

This application claims the benefit of and is a continuation of U.S. patent application Ser. No. 09/981,162 filed on Oct. 17, 2001 now abandoned.

STATEMENT REGARDING FEDERALLY SPONSORED RESEARCH

The present invention was made with Government support under Contract Number F33615-98-3-5103 awarded by the United States Air Force. Accordingly, the United States Government has certain rights in the present invention.

FIELD OF THE INVENTION

The present invention relates generally to testing of bonded structural joints and more particularly to non-destructive testing of bonded joints between composite structures.

BACKGROUND OF THE INVENTION

Bonded joints are widely used in a variety of structural applications, and more specifically, primary composite structures are often bonded together in select aerospace applications. Generally, the strength of the bonded joint between composite structures must be known and certifiable if the bonded joint is used in a primary structure application. Conventional measurement of bond strength generally involves static and dynamic proof testing of entire structural assemblies, wherein several joints and structures are subjected to simulated loads and are monitored for strain levels, which are then correlated to strength values. The structure that is tested, however, is generally a test article and is not used in the final assembly of the aircraft. Further, smaller component testing of individual bonded joints is conducted, but the components are also test articles and are not a part of the operational vehicle structure. Moreover, the smaller components are most frequently destructively tested.

Non-destructive testing methods exist for composite structures, however, the non-destructive methods generally detect the presence of a defect such as a delamination or a foreign object within a laminate, not the strength thereof. Such methods may include, for example, ultrasonics, x-rays, and acoustics, among others commonly known in the art. Unfortunately, non-destructive testing methods to determine the bond strength of composite joints that are a part of a "fly-away" vehicle structure have not been developed to date in systems of the known art.

Methods have been developed to measure the strength of complete joints. However, the methods generally include the need to embed a foreign object within the composite materials in order to measure strength values. For example, U.S. Pat. No. 6,004,817 to Chamberlain et. al. discloses a method for measuring stress levels in polymeric compositions, including adhesively bonded joints. The stress levels are measured by detecting the magnetic characteristics of embedded microparticles that are dispersed uniformly throughout the composition.

Accordingly, there remains a need in the art for a non-destructive test method and system for bonded primary structures that determines the strength of a bonded joint. The system should be capable of non-destructively testing bonded joints that are a part of an operational structural system and should further be capable of testing a bonded joint under a variety of simulated load conditions.

SUMMARY OF THE INVENTION

In one form, the present invention provides a method for measuring bonded joint strength wherein a source of rapid surface pressure application is positioned adjacent a bonded assembly and is activated to excite a surface of the bonded assembly containing the bonded joint to create a shock load. The shock load creates compression and then tension within the bonded joint, in addition to surface motions proximate the bonded assembly. The resulting surface motions are then measured with a surface motion detector, and the surface motions are correlated with the internal tensile stress and are further used to determine whether or not the bond failed. Accordingly, a non-destructive method of testing the strength of a bonded joint is provided in accordance with the teachings of the present invention.

In another form of the present invention, a bond strength measurement system is provided that uses a piston activated by an electromagnetic launcher as a source of rapid surface pressure application. Generally, the piston is activated to impact a surface of the bonded assembly proximate the bonded joint, wherein a shock load therefrom produces a compressive wave through the thickness of the bonded joint. When the compressive wave reaches outer surfaces of the bonded part, tension waves propagate back through the bonded joint, thereby creating translaminar tension at a bond line between two components, more specifically composite structures, which are bonded together. The impact also produces surface motions proximate the bonded joint that are measured using a surface motion detector such as a laser interferometer. The surface motions are then used to determine whether the bonded joint failed. Further, the tension that is created in the bondline may be varied, as more fully described below, to simulate a variety of load conditions.

In yet another form, an alternate bond strength measurement system is provided that uses a laser as a source of rapid surface pressure application. Accordingly, a laser exciter activates the laser to impact an outer surface of the bonded assembly, which creates a shock load that generates compression and then tension through the bonded joint as previously described. Surface motions are also similarly produced, which are measured and are used to determine the minimum strength of the bonded joint.

In other forms of the present invention, a source of rapid surface pressure application other than a projectile may be employed. For example, the source of rapid surface pressure application may comprise sheet explosives or electrically-produced exploding foils, among others. Generally, the shock load should occur quickly enough to propagate successive compression and tension loads through the bonded joint. Accordingly, other methods commonly known in the art may also be employed to generate the shock loads at the bonded assembly in accordance with the teachings of the present invention.

Although the present invention is directed at determining the strength of a bonded joint between two composite structures, the teachings of the present invention may also be applied to bonded joints with structures having other than composite materials or to a bonded joint between a composite structure and a structure of, for example, titanium or aluminum. Accordingly, the reference to the strength of a bonded joint between two composite structures shall not be construed as limiting the scope of the present invention. Furthermore, the application to aerospace structures shall not be construed as limiting the scope of the present invention.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiments is merely exemplary in nature and is in no way intended to limit the invention, its application, or uses.

In one form, a method for measuring bonded joint strength is provided that generally comprises positioning a source of rapid surface pressure application adjacent a bonded assembly, and activating the source to impact a surface of the bonded assembly containing the bonded joint with rapid pressure to create a shock load. The resulting shock load first creates compression and then tension within the bonded joint, in addition to surface motions proximate the bonded assembly. Accordingly, the surface motions are measured with a surface motion detector and are used to determine the minimum strength of the bonded joint.

Figure 1:
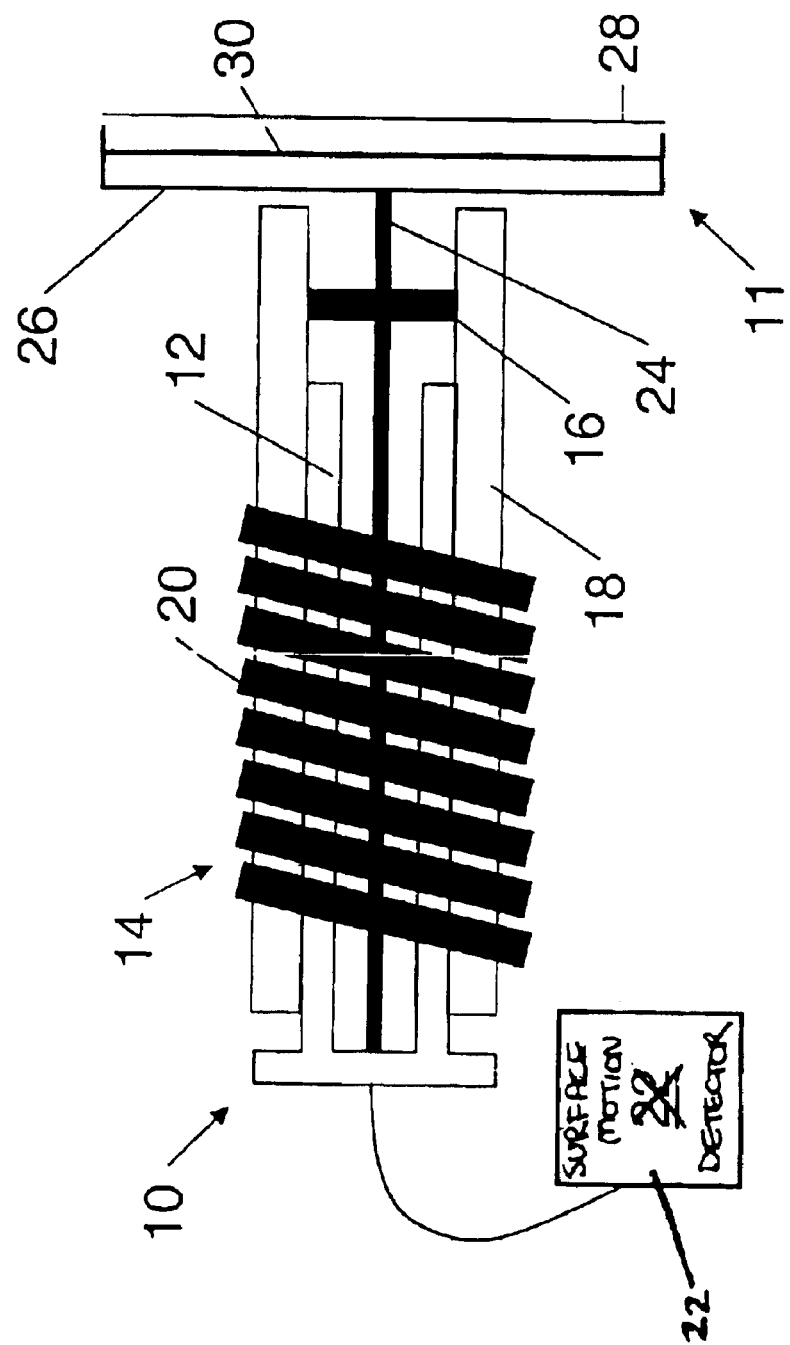
FIG. 1 is a side view of a bond strength measurement system in accordance with one form of the present invention.

A bond strength measurement system according to the methods of the present invention is illustrated and generally indicated by reference numeral 10 in FIG. 1. The bond strength measurement system 10 uses a mechanical impact as a source of rapid surface pressure application, which generally comprises a piston 12 activated by an electromagnetic launcher 14 and a flyer plate 16. As shown, the electromagnetic launcher 14 comprises a hollow guide tube 18, in which the piston 12 is disposed, and exterior coils 20 that generate electromagnetic forces to activate the piston 12. Further, a surface motion detector 22 operates through the hollow guide tube 18 to measure the surface response of a bonded assembly 11 after impact by the piston 12.

Although the surface motion detector 22 is shown disposed on the same side of the bonded assembly 11 as the source of rapid surface pressure application, the surface motion detector 22 may alternately be positioned on an opposite side of the bonded assembly 11 (not shown). Accordingly, the position of the surface motion detector 22 as illustrated herein shall not be construed as limiting the scope of the present invention.

Preferably, the surface motion detector 22 is a VISAR (Velocity Interferometer System for Any Reflector), which measures velocity on the surface of the bonded assembly 11. As shown, the VISAR equipment operates through the guide tube 18 of the electromagnetic launcher 14 and includes a laser diagnostic beam 24 that measures the surface velocity. From the velocity data, the translaminar tension loads may be determined, along with internal failure of the bonded assembly 11.

Additionally, the flyer plate 16 maximizes the transfer of tensile loads from the piston 12 to the bonded assembly 11 with a relatively wide surface area as shown. Alternately, a protective element (not shown) may be disposed between the flyer plate 16 and an outer surface 26 of the bonded assembly 11 to prevent surface damage.

In operation, the bond strength measurement system 10 is positioned adjacent the bonded assembly 11 as shown, and then the exterior coils 20 are activated to create an electromagnetic force that propels the piston 12 and/or the flyer plate 16 against the outer surface 26, which imparts a shock load in the bonded assembly 11. The shock load creates a system of compression and tension waves consistent with the teachings of shock propagation in solids that combine to form a state of tensile stress through the bonded assembly 11. As a result, a translaminar tension load is created at a bonded joint 30 within the bonded assembly 11, which correlates with a specific load condition that the bonded joint 30 is subjected to during operation.

Furthermore, the compression and tension waves cause surface motions (not shown) proximate the bonded assembly 11. Accordingly, the surface motion detector 22 detects and measures the surface motions, which are then correlated to the magnitude of the tensile stress used to determine the minimum strength of the bonded joint 30, or whether the bonded joint 30 failed as a result of the induced stress.

Figure 2:
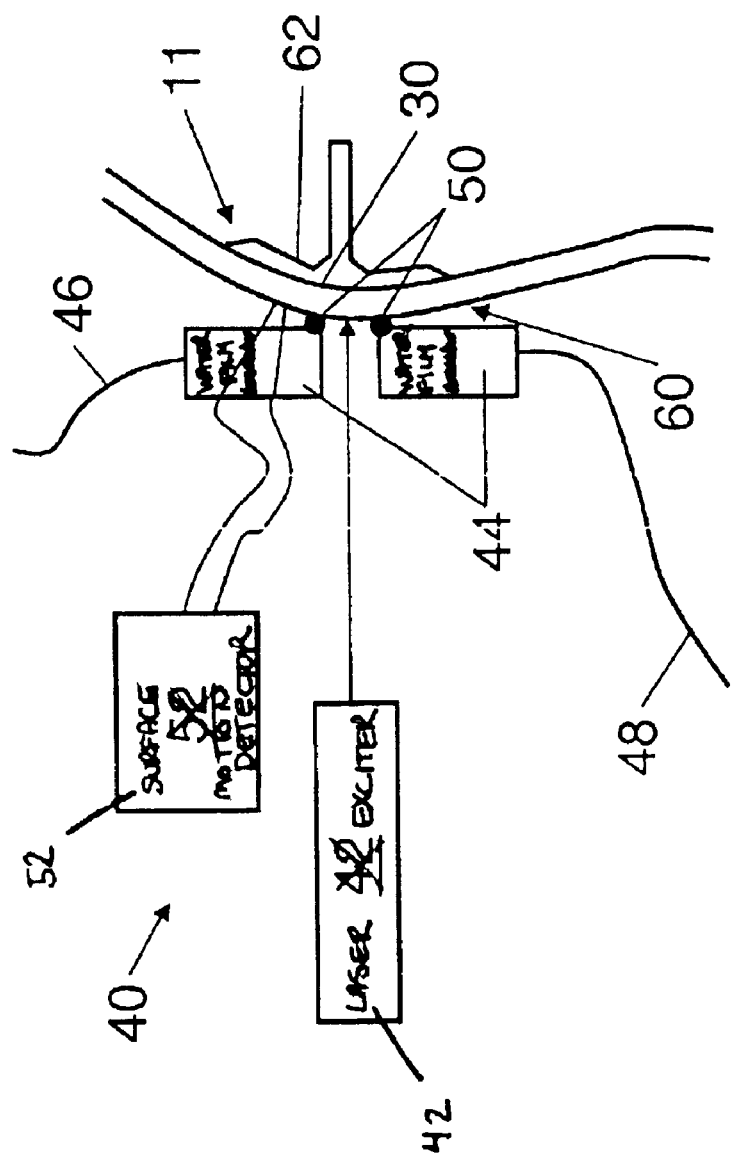
FIG. 2 is a side view of a bond strength measurement system in accordance with another form of the present invention.

In another form, an alternate bond strength measurement system according to the methods of the present invention is illustrated and generally indicated by reference numeral 40 in FIG. 2. The bond strength measurement system 40 uses a laser as a source of rapid surface pressure application, which generally comprises a laser exciter 42 for rapid surface heating and a water film generator 44, which provides pressure confinement proximate the impact area. Additionally, the water film generator 44 comprises with a water feed 46 and a water out 48 to enhance surface pressure generation by the laser exciter 52. Alternately, dry methods of pressure confinement to enhance surface pressure may be employed rather than the water film generator 44.

As further shown, the bond strength measurement system 40 also incorporates a surface motion detector 52, preferably VISAR, that is used to measure velocity on the surface of the bonded assembly 11 as previously described. Accordingly, the translaminar tension loads may be determined, along with failure of the bonded joint 30, from the measured velocity data.

In operation, the bond strength measurement system 40 is positioned adjacent a bonded assembly 11 as shown, and then the laser exciter 42 is activated to impact an outer surface 60, which imparts a shock load against the bonded assembly 11. As previously described, the shock load first creates a compression wave (not shown) that travels through the bonded assembly 11 to a back surface 62, which results in a tension wave (not shown) that travels back through the bonded assembly 11, wherein surface motions (not shown) are created proximate the bonded assembly 11. Similarly, the surface motions are measured with the VISAR 52 to determine translaminar tension loads and failure of the bonded joint 30.

Accordingly, a non-destructive test method and system for bonded primary structures is provided that determines the minimum strength of the bonded joint. The system and method non-destructively test bonded joints that are a part of an operational structure and are further capable of testing a bonded joint under a variety of simulated load conditions. Moreover, the system is portable and may be employed in a variety of locations such as in a manufacturing facility or in a field of operation.

The description of the invention is merely exemplary in nature and, thus, variations that do not depart from the substance of the invention are intended to be within the scope of the invention. Such variations are not to be regarded as a departure from the spirit and scope of the invention.

What is claimed is:

1. A method for measuring bonded joint strength, the method comprising the steps of:
    (a) positioning a source of rapid surface pressure application adjacent a bonded assembly;
    (b) activating the source of rapid surface pressure application to impact the bonded assembly containing the bonded joint with a rapid pressure to create a shock load, wherein the shock load creates compression and then tension within the bonded joint and surface motions proximate the bonded assembly;
    (c) measuring the surface motions with a surface motion detector; and
    (d) correlating the surface motions with the minimum strength of the bonded joint; and
    wherein the surface motion detector includes a laser interferometer.

2. The method of claim 1, further comprising the step of adjusting the rapid pressure to vary the tension within the bonded joint.

3. The method of claim 1, wherein the source of rapid surface pressure application comprises a mechanical impact.

4. The method of claim 3, further comprising the step of activating the mechanical impact with an electromagnetic launcher.

5. The method of claim 3, further comprising the step of activating the mechanical impact with a pressurized gas.

6. The method of claim 3, further comprising the step of activating the mechanical impact with explosives.

7. The method of claim 1, wherein the source of rapid surface pressure application comprises sheet explosives.

8. The method of claim 1, wherein the source of rapid surface pressure application comprises exploding foils.

9. The method of claim 1, wherein the source of rapid surface pressure application comprises a laser.

10. A method for measuring bonded joint minimum strength, the method comprising the steps of:
    (a) generating internal stress leading to surface motions proximate a bonded assembly;
    (b) measuring the surface motions;
    (c) correlating the surface motions with the minimum strength of the bonded joint; and
    wherein the surface motions are measured with a laser interferometer.

11. The method of claim 10, wherein the surface motions are generated by a mechanical impact.

12. The method of claim 11, the mechanical impact is activated by an electromagnetic launcher.

13. The method of claim 11, wherein the mechanical impact is activated by pressurized gas.

14. The method of claim 11, wherein the mechanical impact is activated by explosives.

15. The method of claim 10, wherein the surface motions are generated by sheet explosives.

16. The method of claim 10, wherein the surface motions are generated by exploding foils.

17. The method of claim 10, wherein the surface motions are generated by a laser.

18. A system for measuring bonded joint strength, the system comprising:
    a source of rapid surface pressure application;
    a surface motion detector;
    wherein when the source of rapid surface pressure application is positioned adjacent a bonded assembly and activated to impart a rapid pressure on a surface of the bonded assembly containing the bonded joint to create a shock load, such that the shock load generates compression and then tension within the bonded joint and surface motions proximate the bonded assembly, and the surface motion detector measures the surface motions to determine the minimum strength of the bonded joint; and
    wherein the surface motion detector comprises a laser interferometer.

19. The system of claim 18, wherein the rapid pressure is adjusted such that the amount of tension generated within the bonded joint is varied according to load conditions.

20. The system of claim 18, wherein the source of rapid surface pressure application is a mechanical impact.

21. The system of claim 20, wherein the mechanical impact is activated by an electromagnetic launcher.

22. The system of claim 20, wherein the mechanical impact is activated by pressurized gas.

23. The system of claim 20, wherein the mechanical impact is activated by explosives.

24. The system of claim 18, wherein the source of rapid surface pressure application is sheet explosives.

25. The system of claim 18, wherein the source of rapid surface pressure application is exploding foils.

26. The system of claim 18, wherein the source of rapid surface pressure application comprises a laser.

27. The system of claim 26 further comprising a containment system to enhance surface pressure proximate an impact area.

28. The system of claim 27, wherein the containment system further comprises a water film generator.

29. The system of claim 18 wherein the laser interferometer comprises a Velocity Interferometer System for Any Reflector (VISAR).

30. A system for measuring bonded joint strength, the system comprising:
    (a) a source for generating internal stress;
    (b) a device for measuring surface motion;
    wherein when the source for generating internal stress is activated to impart internal stress in the bonded joint, compression and then tension forces within the bonded joint cause surface motions that are measured by said device for measuring surface motion;
    wherein said device for measuring surface motion includes a laser interferometer.

31. The system of claim 30, wherein the source of generating internal stress comprises a mechanical impact device.

32. The system of claim 31, wherein said source of generating internal stress is activated by an electromagnetic launcher.

33. The system of claim 30, wherein said source of generating internal stress is activated by pressurized gas.

34. The system of claim 30, wherein said source for generating internal stress is activated by explosives.

35. The system of claim 30, wherein said source of generating internal stress includes sheet explosives.

36. The system of claim 30, wherein the source of generating internal stress includes exploding foils.

37. The system of claim 30, wherein the source of generating internal stress includes a laser.

38. The system of claim 30, further comprising a containment system to enhance surface pressure proximate an impact area.

39. The system of claim 38, wherein said containment system further comprises a water film generator.

40. The system of claim 30, wherein said laser interferometer comprises a Velocity Interferometer System for Any Reflector (VISAR).

* * * * *